US010244923B2

(12) United States Patent
Tomiyama

(10) Patent No.: US 10,244,923 B2
(45) Date of Patent: Apr. 2, 2019

(54) JOINING STRUCTURE, JOINING METHOD, AND METHOD OF MANUFACTURING RESIN MEMBER FOR JOINING STRUCTURE

(71) Applicant: Olympus Corporation, Tokyo (JP)

(72) Inventor: Takuji Tomiyama, Hachioji (JP)

(73) Assignee: Olympus Corporation, Tokyo (JP)

( * ) Notice: Subject to any disclaimer, the term of this patent is extended or adjusted under 35 U.S.C. 154(b) by 680 days.

(21) Appl. No.: 14/514,912

(22) Filed: Oct. 15, 2014

(65) Prior Publication Data

US 2015/0031949 A1     Jan. 29, 2015

Related U.S. Application Data

(63) Continuation of application No. PCT/JP2013/073674, filed on Sep. 3, 2013.

(30) Foreign Application Priority Data

Sep. 19, 2012   (JP) ................ 2012-206273

(51) Int. Cl.
| | |
|---|---|
| A61B 1/00 | (2006.01) |
| A61B 17/34 | (2006.01) |
| A61B 1/018 | (2006.01) |
| A61B 17/00 | (2006.01) |
| B29L 31/00 | (2006.01) |
| B29C 39/34 | (2006.01) |

(52) U.S. Cl.
CPC ........ *A61B 1/00128* (2013.01); *A61B 1/0011* (2013.01); *A61B 1/018* (2013.01); *A61B 17/3478* (2013.01); *A61B 2017/00477* (2013.01); *A61B 2017/00526* (2013.01); *B29C 39/34* (2013.01); *B29L 2031/7546* (2013.01); *Y10T 29/49826* (2015.01)

(58) Field of Classification Search
None
See application file for complete search history.

(56) References Cited

U.S. PATENT DOCUMENTS

| 4,721,586 A * | 1/1988 | Kakii ............... B29D 11/00663 |
| | | 264/1.25 |
| 5,151,960 A * | 9/1992 | Warner ................. B29C 33/123 |
| | | 385/53 |
| 2010/0239380 A1 | 9/2010 | Amirov et al. |

FOREIGN PATENT DOCUMENTS

| JP | S53-49884 A | 5/1978 |
| JP | S59-84385 A | 5/1984 |
| | (Continued) | |

OTHER PUBLICATIONS

Japanese Office Action dated Feb. 7, 2017 with English translation for corresponding Japanese application.
(Continued)

*Primary Examiner* — Anthony Calandra
*Assistant Examiner* — Mohammad M Ameen
(74) *Attorney, Agent, or Firm* — Arent Fox LLP

(57) ABSTRACT

A joining structure includes a first member having a cylindrical hollow portion, and a second member that is cylindrical in shape, has an outer circumferential diameter equal to or larger than a diameter of the hollow portion, and is to be pressed into the hollow portion. A concave portion, which is cut out inward from an outer circumference of the first member, is formed on part of a portion of the first member into which the second member is pressed.

9 Claims, 10 Drawing Sheets

(56) References Cited

FOREIGN PATENT DOCUMENTS

| JP | H11-192711 A | | 7/1999 | |
|---|---|---|---|---|
| JP | H11-223163 A | | 8/1999 | |
| JP | 2000-146044 A | * | 5/2000 | |
| JP | 2008-95765 A | | 4/2008 | |
| JP | 2010-533518 A | | 10/2010 | |
| JP | 2011-042141 A | | 3/2011 | |
| WO | WO 2009015672 A1 | * | 2/2009 | ........... A61B 17/164 |

OTHER PUBLICATIONS

Japanese Office Action dated Aug. 23, 2016 with English translation for corresponding Japanese application.
International Search Report issued for PCT/JP2013/073674, dated Dec. 10, 2013.

* cited by examiner

JOINING STRUCTURE, JOINING METHOD, AND METHOD OF MANUFACTURING RESIN MEMBER FOR JOINING STRUCTURE

CROSS REFERENCES TO RELATED APPLICATIONS

This application is a continuation of PCT international application Ser. No. PCT/JP2013/073674 filed on Sep. 3, 2013 which designates the United States, incorporated herein by reference, and which claims the benefit of priority from Japanese Patent Application No. 2012-206273, filed on Sep. 19, 2012, incorporated herein by reference.

BACKGROUND OF THE INVENTION

1. Field of the Invention

The present invention relates to a joining structure for joining pipes in a treatment tool for use in an endoscope, for example, a joining method, and a method of manufacturing a resin member for the joining structure.

2. Description of the Related Art

In the field of medicine, endoscope systems have conventionally been used to observe organs in subjects such as patients. Some of such endoscope systems are known to include a flexible and elongated insertion portion that is to be inserted into the body cavity of the subject, an imaging element that is provided at the distal end of the insertion portion to capture an in-vivo image, and an external device that is connected to the insertion portion via a cable to perform image processing on the in-vivo image taken by the imaging element and displays the in-vivo image on a display unit or the like. Doctor or the like can insert a treatment tool into the insertion portion and operate the same while watching the in-vivo image captured by the imaging element, thereby to apply specified treatment to the inside of the subject's body.

Examples of the treatment tools for use in the endoscope system include a syringe. The syringe is formed by pressing a pipe to be inserted into the insertion portion, into the inside of a pipe grasped by a doctor or the like to join the pipes (for example, refer to Japanese Patent Application Laid-open No. 53-49884).

The syringe may also be made of resin and metal. To join such a resin and metal, there has been disclosed a technique for pressing a metal pipe into a hollow portion of a resin molded product in which the hollow portion is formed (for example, refer to Japanese Patent Application Laid-open No. 11-223163). However, the resin molded product has a problem that the diameter of the hollow portion are changed by sink marks (recessions on a thick surface) during the molding, which leads to reduction in airtightness between the pipes.

In this regard, to improve airtightness between the pipes, there has been disclosed a technique for reducing a resin molded product in thickness by forming a hollow space between its outer circumference and hollow portion, thereby to suppress occurrence of sink marks on the resin molded product during the molding (for example, refer to Japanese Patent Application Laid-open No. 59-84385).

There has also been disclosed a technique for suppressing warpage of a molded product by adjusting the cutting position of a gate as a resin inlet and the amount of a resin (for example, refer to Japanese Patent Application Laid-open No. 11-192711). According to the technique disclosed in Japanese Patent Application Laid-open No. 11-192711, a molding process is carried out such that a resin is poured via an opening extended along a longitudinal direction of the molded product, from a direction orthogonal to the longitudinal direction of the molded product.

SUMMARY OF THE INVENTION

A joining structure according to one aspect of the invention includes: a first member having a cylindrical hollow portion; and a second member that is cylindrical in shape, has an outer circumferential diameter equal to or larger than a diameter of the hollow portion, and is to be pressed into the hollow portion. A concave portion, which is cut out inward from an outer circumference of the first member, is formed on part of a portion of the first member into which the second member is pressed.

A joining method according to another aspect of the invention is a joining method for joining a first member having a cylindrical hollow portion, and a second member that is cylindrical in shape, has an outer circumferential diameter equal to or larger than a diameter of the hollow portion, and is to be pressed into the hollow portion. The method includes: a concave forming step of forming a concave portion, which is cut out inward from an outer circumference of the first member, on part of a portion of the first member into which the second member is to be pressed; and a pressing step of pressing the second member into the hollow portion.

A method of manufacturing a resin member for joining structure according to still another aspect of the invention is a method of manufacturing a resin member for joining structure having a hollow portion into which a cylindrical member is pressed for joining. The method includes molding the resin member by pouring a liquid resin constituting the resin member into a metal mold from a portion different from a portion into which the cylindrical member is to be pressed, and then solidifying the liquid resin.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
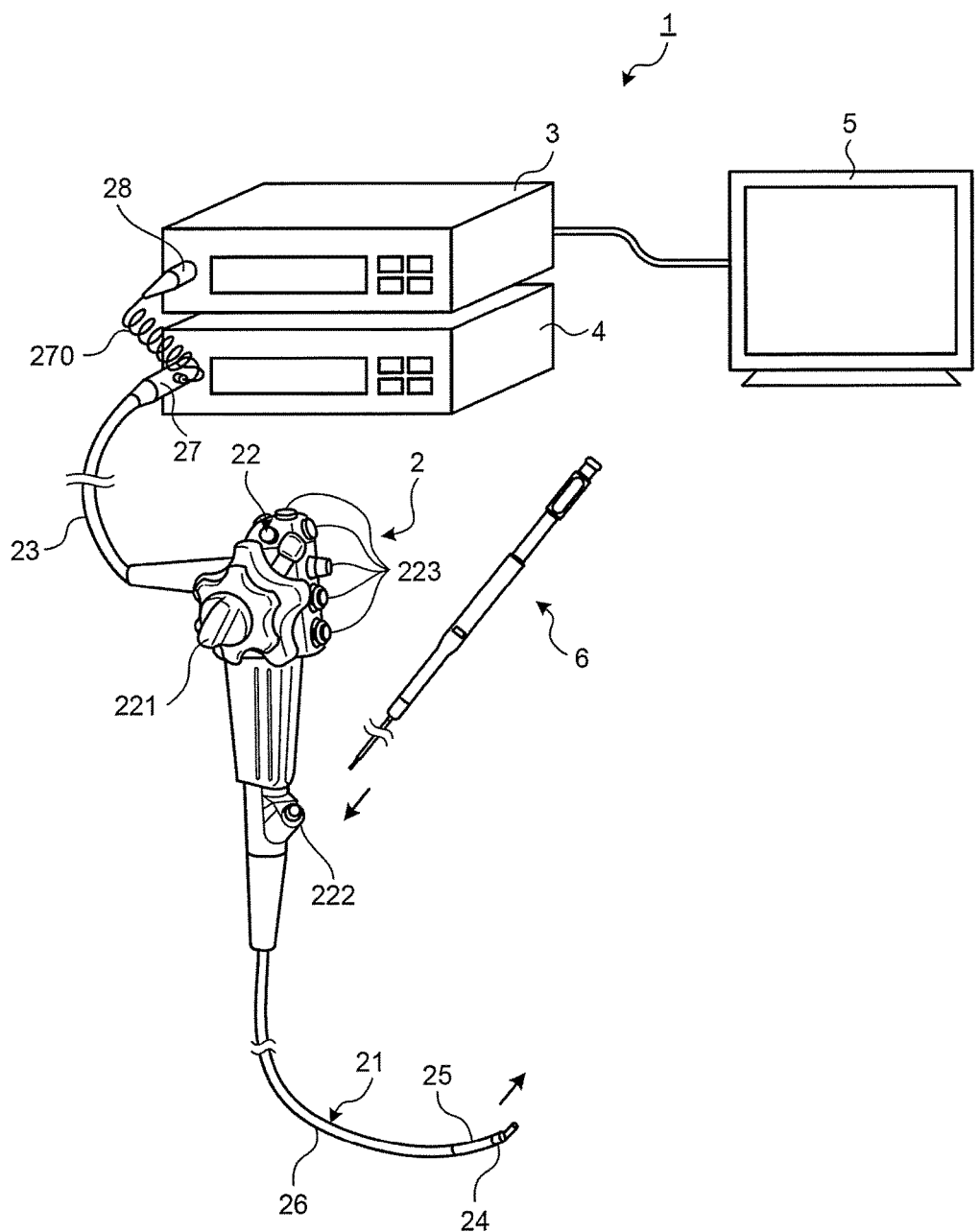
FIG. 1 is a diagram illustrating a general configuration of an endoscope system according to an embodiment of the present invention.

As modes for carrying out the present invention (hereinafter, referred to as "embodiment"), a medical endoscope system for capturing and displaying an image of body cavity of a subject such as a patient will be described below. The present invention is not limited to the embodiment. The same reference signs are used to refer to the same elements throughout the drawings. It is noted that the drawings are schematic and the relationship between thickness and width of respective members and the ratios among the members illustrated in the drawings may differ from actual ones. In addition, the dimensions and ratios may be differently illustrated among the drawings.

FIG. 1 is a diagram illustrating a general configuration of an endoscope system 1 according to the embodiment of the present invention. As illustrated in FIG. 1, the endoscope system 1 includes: an endoscope 2 having a distal end portion to be inserted into a body cavity of a subject to capture an in-vivo image of the subject; a control device 3 that performs specified image processing on the in-vivo image captured by the endoscope 2 and controls centrally operations of the entire endoscope system 1; a light source device 4 that generates illumination light to be emitted from the distal end of the endoscope 2; a display device 5 that displays the in-vivo image having undergone the image processing by the control device 3; and a treatment tool 6 that has at a distal end thereof a biopsy forceps, a laser knife, an inspection probe or the like and is inserted into the endoscope 2 and let itself out from the distal end of a distal end portion 24.

The endoscope 2 includes: a flexible and elongated insertion portion 21; an operation portion 22 that is connected to a proximal end side of the insertion portion 21 to receive input of various operation signals; and a universal cord 23 that is extended from the operation portion 22 in a direction different from the direction of extension of the insertion portion 21 and has therein various cables for connection with the control device 3 and the light source device 4.

The insertion portion 21 includes: the distal end portion 24 with an imaging element therein; a curve portion 25 that is capable of free curve and formed by a plurality of curve pieces; and an elongated flexible tube portion 26 that is provided at a proximal end side of the curve portion 25.

The imaging element receives external light, subjects the external light to photoelectric conversion into an electric signal, and performs specified signal processing on the signal. The imaging element is implemented using a CCD image sensor or a CMOS image sensor, for example.

An assembled cable having a plurality of bound signal lines is connected between the operation portion 22 and the distal end portion 24 to send electric signals to or receive the same from the control device 3. The plurality of signal lines includes a signal line for transmitting an image signal output from the imaging element to the control device 3, a signal line for transmitting a control signal output from the control device 3 to the imaging element, or the like.

The operation portion 22 includes: a curve knob 221 that curves the curve portion 25 in vertical and horizontal directions; a treatment tool insertion portion 222 that allows the treatment tool 6 such as a biopsy forceps, a laser knife, or an inspection probe to be inserted into the body cavity; and a plurality of switches 223 as an operation input unit for inputting operation instructive signals for the control device 3, the light source device 4, and peripheral devices such as an air feeding means, a water feeding means, or a gas feeding means.

The universal cord 23 has therein at least a light guide and an assembled cable. Provided at an end portion of a side of the universal cord 23 opposite to the side connected to the operation portion 22 are a connector portion 27 detachably attached to the light source device 4 and an electric connector portion 28 that is electrically connected to the connector portion 27 via a coiled coil cable 270 and is detachably attached to the control device 3.

The control device 3 generates an in-vivo image to be displayed on the display device 5, based on image signals in parallel mode output from the distal end portion 24. The control device 3 performs white balance (WB) adjustment process, gain adjustment process, gamma correction process, D/A conversion process, format change process, and the like, for example.

The light source device 4 includes a light source, a rotary filter, and a light source control unit, for example. The light source is configured by a white light emitting diode (LED), a xenon lamp, or the like. The light source generates white light under control of the light source control unit. The light generated by the light source is radiated from the distal end of the distal end portion 24 through the light guide.

The display device 5 has the function of receiving the in-vivo image generated by the control device 3 from the control device 3 via an image cable and displaying the same. The display device 5 is configured by liquid crystal or organic electro luminescence (EL), for example.

Figure 2:
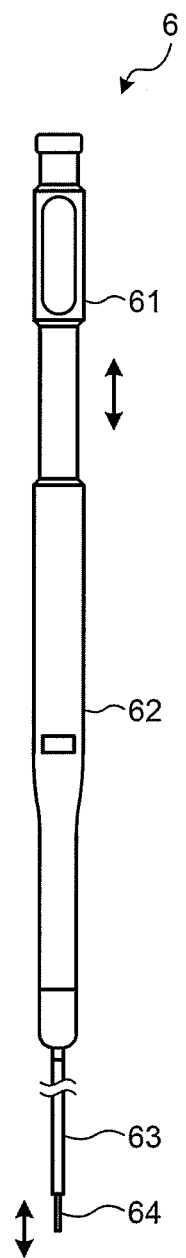
FIG. 2 is a schematic view illustrating a general configuration of a treatment tool included in the endoscope system according to the embodiment of the present invention.

FIG. 2 is a schematic view illustrating a general configuration of the treatment tool 6 included in the endoscope system 1 according to the embodiment of the present invention. The treatment tool 6 is a syringe that discharges a drug solution or the like or absorbs a body fluid from the subject, for example. The treatment tool 6 includes: an almost rod-shaped piston 61 (first member or resin member for joining structure); a cylindrical portion 62 that has at one end thereof a hollow portion with an inner diameter according to an outer diameter of a portion of the piston 61; an elongated flexible tube portion 63 that has one end connected to the cylindrical portion 62; and a functional portion 64 that is provided at the other end side of the flexible tube portion 63 and is configured by a syringe needle capable of back-and-forth movement from the end portion of the flexible tube portion 63 according to reciprocation of the piston 61 with respect to the cylindrical portion 62. The treatment tool 6 is disposed in the endoscope 2 such that the flexible tube portion 63 is inserted into the treatment tool insertion portion 222, and the functional portion 64 can be let out from the distal end portion 24.

In the thus configured endoscope system 1, when the flexible tube portion 63 of the treatment tool 6 is inserted into the treatment tool insertion portion 222 of the endoscope 2 and the flexible tube portion 63 is let out from the distal end portion 24 by the action of the piston 61, the functional portion 64 (syringe needle) is inserted into the inner wall surface of the subject for injection of a drug solution. In some cases, the treatment tool 6 may be used to discharge a drug solution or absorb the body fluid without insertion of the needle into the inner wall surface of the subject.

Figure 3:
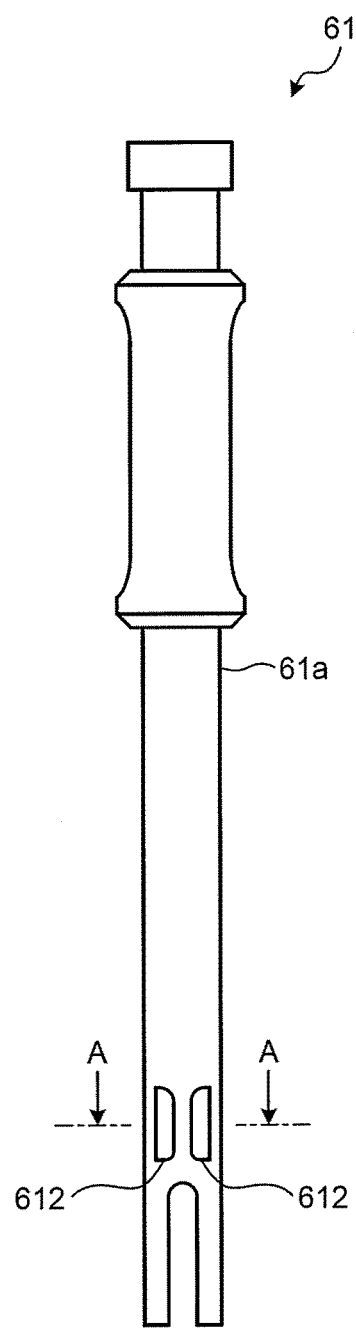
FIG. 3 is a side view illustrating a configuration of main components of the treatment tool included in the endoscope system according to the embodiment of the present invention.
Figure 4:
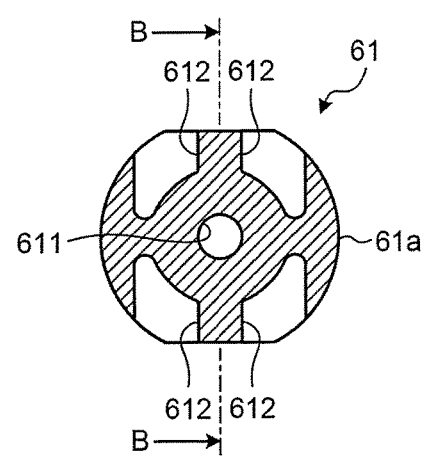
FIG. 4 is a cross-sectional view taken along line A-A of FIG. 3.
Figure 5:
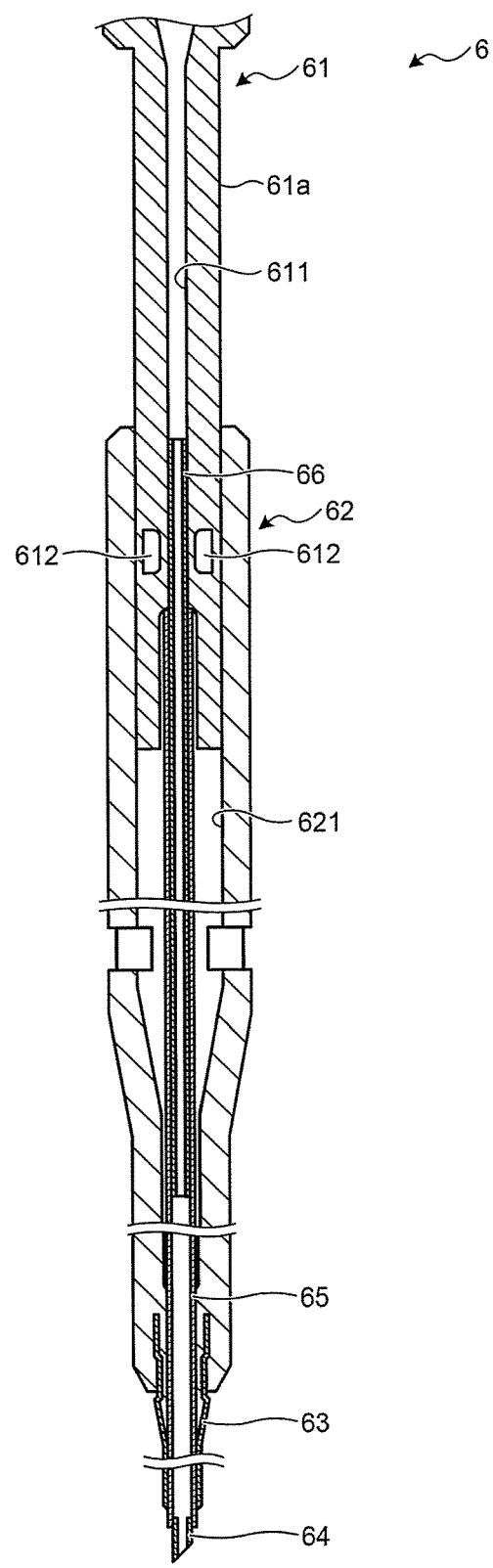
FIG. 5 is a cross-sectional view illustrating a configuration of main components of the treatment tool included in the endoscope system according to the embodiment of the present invention.

FIG. 3 is a side view illustrating a configuration of main components of the treatment tool 6 included in the endoscope system 1 according to the embodiment of the present invention. FIG. 4 is a cross-sectional view taken along line A-A of FIG. 3. FIG. 5 is a cross-sectional view illustrating a configuration of main components of the treatment tool 6 included in the endoscope system 1 according to the embodiment. The treatment tool 6 is provided with connecting tubes 65 and 66 that connect the piston 61 and the functional portion 64.

The piston 61 includes an almost cylindrical main body portion 61a. The main body portion 61a includes: a hollow portion 611 that is extended along the longitudinal direction of the main body portion 61a to form a hollow space in the main body portion 61a; and a plurality of (four in the embodiment) concave portions 612 that is provided on part of the outer circumference of the main body portion 61a and cut out inward from the outer circumference.

The connecting tube 65 is made of a flexible elongated resin material, for example, and is connected to the functional portion 64 at one end. The connecting tube 66 (second member or cylindrical member) is made of a cylindrical metal, for example, and is connected to the piston 61 (hollow portion 611) at one end and connected to the connecting tube 65 at the other end. The resin for use in the connecting tube 65 includes an acrylonitrile butadiene styrene (ABS) resin, for example, and the metal for use in the connecting tube 66 includes a stainless steel such as SUS304, for example. The outer diameter of the connecting tube 66 is equal to or larger than the diameter of the hollow portion 611 and the inner diameter of the connecting tube 65 so that the connecting tube 66 can be pressed into the hollow portion 611 and the connecting tube 65.

The connecting tube 66 is inserted into the hollow portion 611 at one end, and is inserted into the connecting tube 65 at the other end. The connecting tube 66 is pressed into and connected to both of the hollow portion 611 and the connecting tube 65. At that time, the connecting tube 66 is joined to the main body portion 61a with the concave portions 612 formed at the molding. Specifically, the treatment tool 6 is manufactured by forming the concave portions on the outer circumference of the piston 61 according to the pressing position of the connecting tube 66 (concave forming step) and then pressing the connecting tube 66 into the hollow portion 611 (pressing step).

The piston 61 is connected to the connecting tube 65 at one end of the main body portion 61a via the connecting tube 66, and is connected to a hollow portion 621 of the cylindrical portion 62 so as to be capable of back-and-forth movement. At that time, except for the end portion (distal end) of the connecting tube 65 at the side different from the piston 61 side, the connecting tube 65 is inserted into the hollow portion 621 and the flexible tube portion 63. A tube for transporting a drug solution, a container for holding a drug solution, or the like is attached to the other end of the piston 61.

The plurality of concave portions 612 is provided on part of a portion of the main body portion 61a into which the connecting tube 66 is pressed. This makes it possible to suppress occurrence of sink marks on the hollow portion 611 according to the forming positions of the concave portions 612 of the main body portion 61a during the manufacture of the piston 61, thereby to reduce changes in the opening diameter of the hollow portion 611 and ensure the pressing (fitting) between the hollow portion 611 and the connecting tube 66. In addition, by reducing changes in the opening diameter, it is possible to ensure the contact area between the hollow portion 611 and the connecting tube 66 and maintain the joining state in a further reliable manner.

The plurality of concave portions 612 is preferably provided at positions rotationally symmetric with respect to the central axis of the hollow portion 611. By arranging the plurality of concave portions 612 at positions symmetric to each other, it is possible to reduce changes in the opening diameter of the hollow portion 611 and form the hollow portion 611 more precisely according to the design, and it is also possible to add uniform load to the pressed connecting tube 66. In addition, the concave portions 612 are preferably formed according to the length of insertion of the connecting tube 66 into the hollow portion 611.

Figure 6:
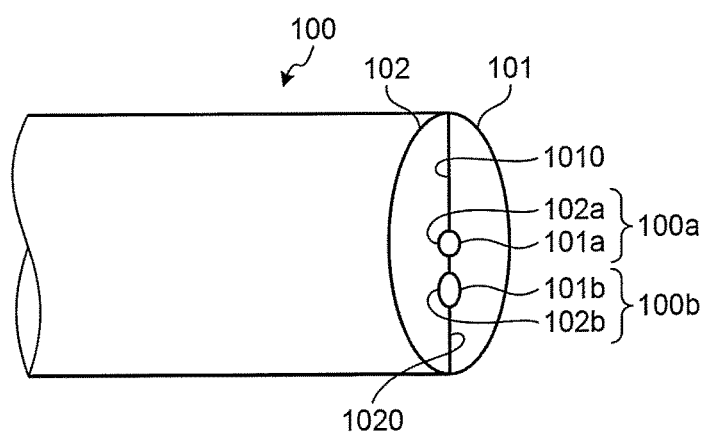
FIG. 6 is a perspective diagram schematically illustrating one example of a method for fabricating a piston of the treatment tool included in the endoscope system according to the embodiment of the present invention.
Figure 7:
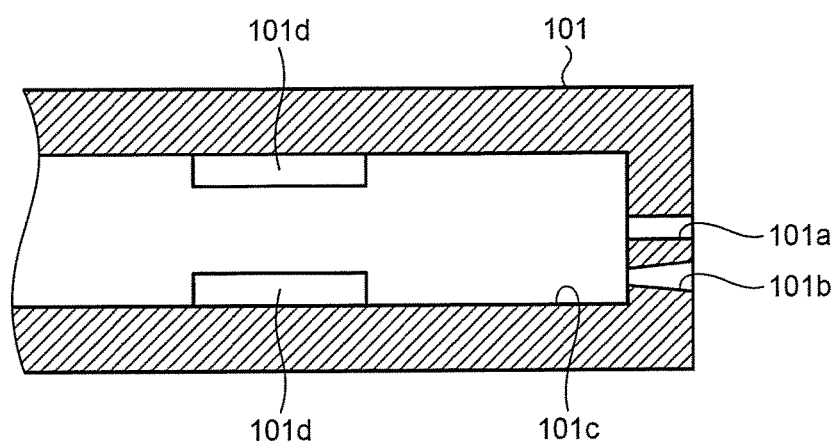
FIG. 7 is a cross-sectional view schematically illustrating one example of a method for fabricating the piston of the treatment tool included in the endoscope system according to the embodiment of the present invention.
Figure 8:
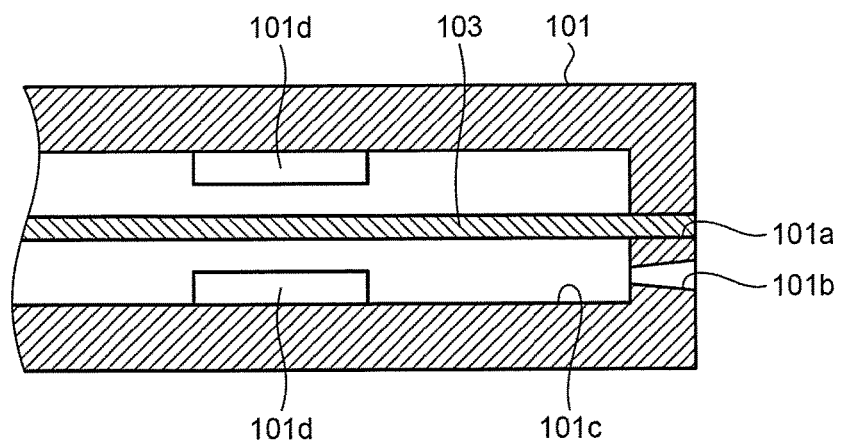
FIG. 8 is a cross-sectional view schematically illustrating one example of a method for fabricating the piston of the treatment tool included in the endoscope system according to the embodiment of the present invention.
Figure 9:
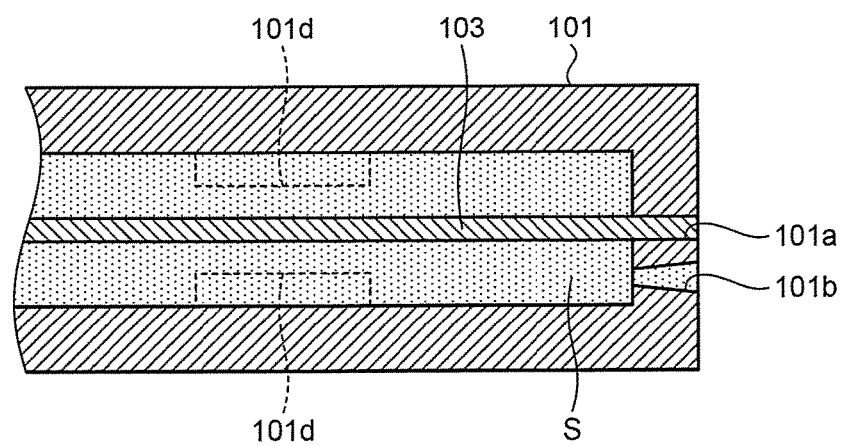
FIG. 9 is a cross-sectional view schematically illustrating one example of a method for fabricating the piston of the treatment tool included in the endoscope system according to the embodiment of the present invention.
Figure 10:
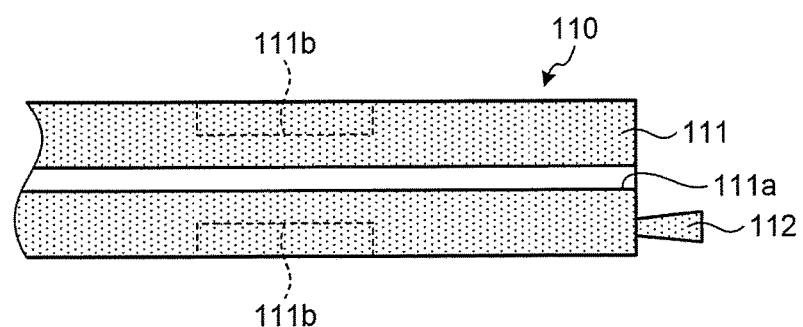
FIG. 10 is a cross-sectional view schematically illustrating one example of a method for fabricating the piston of the treatment tool included in the endoscope system according to the embodiment of the present invention.

Subsequently, a method for fabricating the piston 61 will be described with reference to FIGS. 6 to 10. FIG. 6 is a perspective diagram schematically illustrating one example of a method for fabricating the piston 61 of the treatment tool 6 included in the endoscope system 1 according to the embodiment of the present invention. FIGS. 7 to 10 are cross-sectional views schematically illustrating examples of a method for fabricating the piston 61 of the treatment tool 6 included in the endoscope system 1 according to the embodiment of the present invention. FIGS. 7 to 9 each illustrate a planar cross section in the vicinity of a planar surface portion 1010 described later and in parallel to the planar surface portion 1010. FIG. 10 is a cross section of a molded product of the piston 61 taken along line B-B of FIG. 4.

The piston 61 according to the embodiment is fabricated by injection molding. The metal mold for shaping the piston 61 may be a metal mold 100 as illustrated in FIGS. 6 and 7. The metal mold 100 has two members formed by halving a cylindrical body, for example (a first metal mold constituent member 101 and a second metal mold constituent member 102). The first metal mold constituent member 101 and the second metal mold constituent member 102 are brought into surface contact with each other at the planate planar surface portions 1010 and 1020 to form the metal mold 100. The metal mold 100 includes a first insertion hole 100a into which a core bar is inserted to form the hollow portion 611 and a second insertion hole 100*b* into which a resin is poured to form the piston 61.

The first metal mold constituent member 101 is formed by a columnar member with a semicircular cross section. The first metal mold constituent member 101 includes a first groove portion 101*a* and a second groove portion 101*b* each having an opening in the planar surface portion 1010, and a cutout portion 101*c*.

The first groove portion 101*a* is extended along a longitudinal direction of the first metal mold constituent member 101 from one end of the first metal mold constituent member 101 in the longitudinal direction to constitute a part of the first insertion hole 100*a*. The second groove portion 101*b* is located at a different position from the first groove portion 101*a* and extended along the longitudinal direction of the first metal mold constituent member 101 from the one end of the first metal mold constituent member 101 in the longitudinal direction to constitute a part of the second insertion hole 100*b*.

The cutout portion 101*c* is cut out according to the shape of a part of the outer circumference of the piston 61. The cutout portion 101*c* has convex portions 101*d* having convex shape according to the concave portions 612. The cutout portion 101*c* communicates with the first groove portion 101*a* and the second groove portion 101*b*.

As with the first metal mold constituent member 101, the second metal mold constituent member 102 is also formed by a columnar member with a semicircular cross section, and includes a first groove portion (first groove portion 102*a*) and a second groove portion (second groove portion 102*b*) each having an opening in a planar surface portion 1020, and a cutout portion.

When the first metal mold constituent member 101 and the second metal mold constituent member 102 are brought into surface contact with each other at the planar surface portions 1010 and 1020, the first groove portions, the second groove portions, and the cutout portions form hollow spaces, respectively. Specifically, the first groove portions 101*a* and 102*a* form the foregoing first insertion hole 100*a*, the second groove portions 101*b* and 102*b* form the foregoing second insertion hole 100*b*. In addition, the cutout portions are opposed to each other to form a hollow space (casting mold for the piston 61) according to the outer shape of the piston 61.

To fabricate the piston 61, first, a cored bar 103 is inserted into the first insertion hole 100*a* of the metal mold 100 (refer to FIG. 8). After that, a liquid resin S as an element of the piston 61 is poured into the second insertion hole 100*b*. At that time, the resin S flows from the second insertion hole 100*b* through the casting mold along the longitudinal direction to fill the casting mold (refer to FIG. 9).

After the resin S is filled into the casting mold and solidified, the first metal mold constituent member 101 and the second metal mold constituent member 102 are separated from each other to obtain a molded product 110 as illustrated in FIG. 10. This molding step corresponds to the foregoing concave forming step. The molded product 110 has a molded portion 111 formed according to the casting mold and a tongue piece portion 112 formed according to the hollow space of the second insertion hole 100*b*. In addition, the molded portion 111 has a hollow portion 111*a* formed according to the hollow portion 611 and concave portions 111*b* formed according to the concave portions 612. After the obtainment of the molded product 110, the tongue piece portion 112 is cut out from the molded portion 111 and subjected to fine processing treatment or the like, thereby to obtain the piston 61.

According to the fabricating method described above, since the resin S is poured from one end of a casting mold in a longitudinal direction of the casting mold along the longitudinal direction, the piston 61 can be molded without adverse influence of the pressure of the flowing resin S on the molding of the hollow portion 611. Therefore, it is possible to fabricate the piston 61 with suppression of occurrence of sink marks on the hollow portion 611. The piston 61 may be configured without the concave portions 612 (and the convex portions 101*d*) if the pressure of the flowing resin S has no adverse effect on the molding of the hollow portion 611.

In the fabricating method described above, the resin S is poured into the casting mold from the one end thereof via the second insertion hole 100*b*. However, the pouring position is not limited to the second insertion hole 100*b*. For example, there may be a plurality of pouring positions or the resin may be poured from the direction orthogonal to the longitudinal direction. The pouring position can be any position except for the forming positions of the concave portions 612. In addition, the pouring position is preferably at the end portion of the side different from the side at which the connecting tube 66 is inserted into the hollow portion 611.

Figure 11:
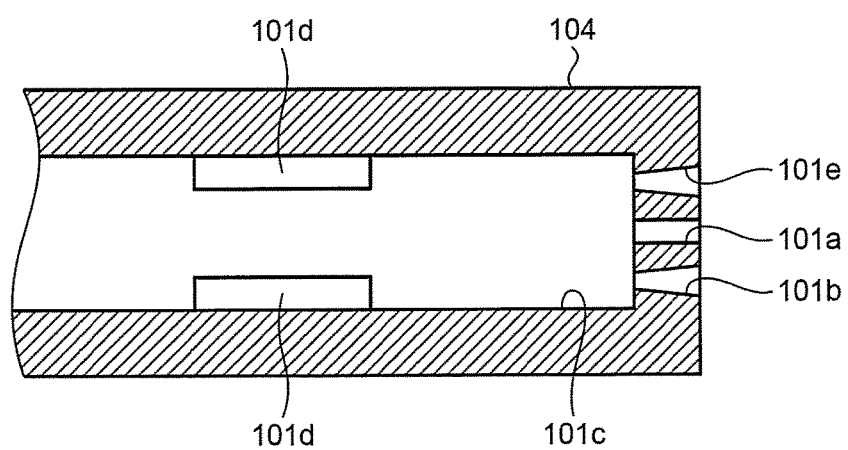
FIG. 11 is a cross-sectional view schematically illustrating another example of a method for fabricating the piston of the treatment tool included in the endoscope system according to the embodiment of the present invention.

FIG. 11 is a cross-sectional view schematically illustrating another example of a method for fabricating the piston 61 of the treatment tool 6 included in the endoscope system 1 according to the embodiment. As illustrated in FIG. 11, a plurality of groove portions (the second groove portion 101*b* and a third groove portion 101*e* in FIG. 11) may be provided at one end of a first metal mold constituent member 104 such that the resin S is poured into each of the insertion holes. The second metal mold constituent member is configured in the same manner as the first metal mold constituent member 104.

Figure 12:
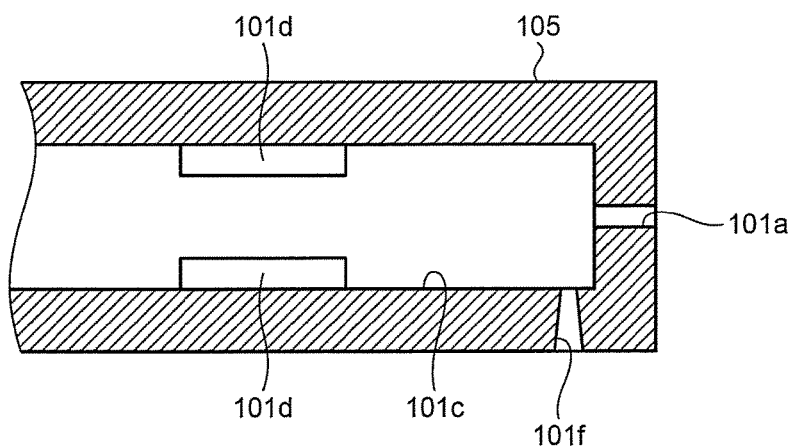
FIG. 12 is a cross-sectional view schematically illustrating another example of a method for fabricating the piston of the treatment tool included in the endoscope system according to the embodiment of the present invention.

FIG. 12 is a cross-sectional view schematically illustrating another example of a method for fabricating the piston 61 of the treatment tool 6 included in the endoscope system 1 according to the embodiment. As illustrated in FIG. 12, the resin S may be poured into a groove portion (a first groove portion 101*f* in FIG. 12) that is provided at one end portion of a first metal mold constituent member 105 and extended in the direction orthogonal to the longitudinal direction. The second metal mold constituent member is configured in the same manner as the first metal mold constituent member 105.

In the case of pouring the resin S from the insertion holes illustrated in FIG. 11 or 12, the resin S can be poured from the one end of the casting mold in the longitudinal direction to mold the piston 61 without adverse influence of pressure of the flowing resin S on the molding of the hollow portion 611. Therefore, it is possible to fabricate the piston 61 with suppression of occurrence of sink marks on the hollow portion 611.

In the foregoing description, the first metal mold constituent member 101 and the second metal mold constituent member 102 each have a semicircular cross section. However, these members may have any outer shape as far as they have an opening for molding. For example, these members may have a square columnar shape or a shape obtained by dividing equally an ellipse.

According to the embodiment described above, the concave portions 612 are provided according to the pressed portion of the connecting tube 66 on part of the outer circumference of the main body portion 61*a* having the hollow portion 611 into which the connecting tube 66 is pressed. It is thus possible to suppress occurrence of sink marks during manufacture of the piston 61 and reduce changes in the opening diameter of the hollow portion 611. This makes it possible to prevent reduction in joining strength between the hollow portion 611 and the connecting tube 66 (between the pipes) while improving airtightness between these components.

In addition, according to the embodiment, the connecting tube 66 is pressed into the hollow portion 611 to be joined to the same. Thus, unlike in conventional joining structures with the use of an adhesive, there is no need to take into account the time for hardening of an adhesive. This makes it possible to shorten the manufacturing time and decrease the manufacturing steps. In addition, the joining structure according to the embodiment allows reduction of manufacturing costs as well as reduction of the manufacturing steps.

In the foregoing description of the embodiment, the four concave portions 612 are provided. However, the number of the concave portions 612 may be one or more as far as the hollow portion 611 is made thinner from the outer circumference of the main body portion 61*a* to reduce changes in the diameter of the hollow portion 611. The size of one concave portion 612 can be arbitrarily designed as well.

Figure 13:
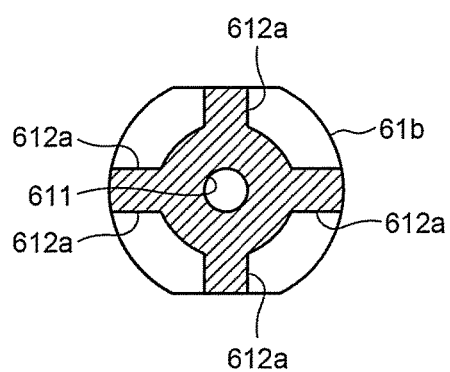
FIG. 13 is a cross-sectional view of a configuration of a treatment tool in an endoscope system according to a first modification of the embodiment of the present invention.

FIG. 13 is a cross-sectional view of a configuration of the treatment tool 6 in the endoscope system 1 according to a first modification of the embodiment. As in a main body portion 61*b* according to the first modification, concave portions 612*a* may be provided to be larger in concave formation area than the concave portions 612 according to the foregoing embodiment. This reduces changes in the diameter of the hollow portion 611 in a more reliable manner.

Figure 14:
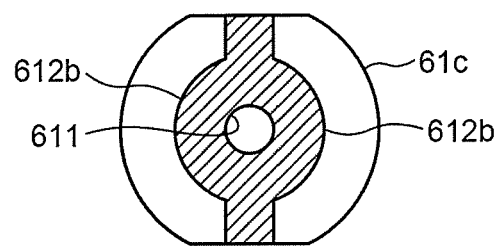
FIG. 14 is a cross-sectional view of a configuration of a treatment tool in an endoscope system according to a second modification of the embodiment of the present invention.

FIG. 14 is a cross-sectional view of a configuration of the treatment tool 6 in the endoscope system 1 according to a second modification of the embodiment. As in a main body portion 61*c* according to the second modification, concave portions 612*b* may be provided to be larger in concave formation area than the concave portions 612*a* according to the foregoing first modification. The concave portions 612*b* are cutouts in an almost semilunar shape with respect to the outer circumference of the main body portion 61*c*. This reduces changes in the diameter of the hollow portion 611 in a more reliable manner.

Figure 15:
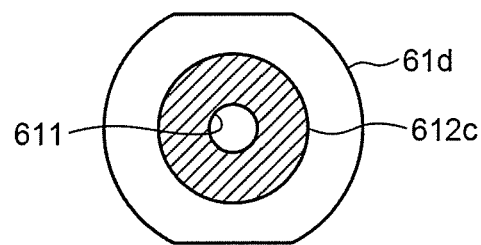
FIG. 15 is a cross-sectional view of a configuration of a treatment tool in an endoscope system according to a third modification of the embodiment of the present invention.

FIG. 15 is a cross-sectional view of a configuration of the treatment tool 6 in the endoscope system 1 according to a third modification of the embodiment. As in a main body portion 61*d* according to the third modification, a concave portion 612*c* may be provided to be larger in concave formation area than the concave portions 612*b* according to the foregoing second modification. The concave portion 612*c* is a cutout in an annular shape with respect to the outer circumference of the main body portion 61*d*. This reduces changes in the diameter of the hollow portion 611 in a more reliable manner.

According to the foregoing embodiment, a resin pipe and a metal pipe are joined together. Alternatively, resin pipes may be joined together. In addition, in the foregoing description, the pipe joining structure according to the embodiment is applied to the treatment tool 6 for use in the endoscope 2 of the endoscope system 1. However, the pipe joining structure according to the embodiment can also be applied to any tool in which a tubular member (or columnar member) is pressed into a hollow portion of a resin main body.

In the forgoing description of the embodiment, a syringe is exemplified as the treatment tool. However, the treatment tool may be applied to any tool with a joining structure, such as a biopsy forceps, laser knife, or measurement probe.

As in the foregoing, the joining structure, joining method, and method of manufacturing a resin member for joining structure according to the present invention are useful in suppressing reduction in joining strength between pipes while improving airtightness between the pipes.

Further advantages and modifications can be readily retrieved by those skilled in the art. Thus, a wider variety of aspects for carrying out the present invention are not limited to the specific details and representative embodiments depicted and described above. Therefore, the present invention can be modified in various manners without deviating from the spirit of general conception or scope of the present invention defined by the attached claims and their equivalences.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for manufacturing a resin member, the method comprising:
    providing a mold with a cylindrical opening defined by a cylindrical inner surface and having a central axis, the mold including a plurality of convex portions extending from the cylindrical inner surface radially inward toward the central axis such that each of the convex portions has a proximal end and a distal end, the convex portions being symmetrical relative to the central axis, at least two of the convex portions extending less than 180 degrees around the central axis and being aligned with one another such that an imaginary plane extending orthogonally to the central axis passes through the at least two convex portions;
    providing an insert along the central axis to form a mold cavity between the insert and the cylindrical inner surface of the mold, the distal ends of the convex portions not extending to the insert such that the mold cavity includes an open space between the distal end of the convex portions and the insert;
    pouring a liquid resin into the mold cavity; and
    solidifying the liquid resin to form a resin member having a central axis corresponding to the central axis of the mold and a cylindrical opening formed by the insert, the resin member having walls whose thickness is defined between an outer surface of the resin member and the cylindrical opening of the resin member, the resin member having a plurality of concave portions formed by the convex portions of the mold and being symmetrical relative to the central axis of the resin member, the concave portions not extending into the cylindrical opening and causing the thickness of the walls of the resin member to be reduced at the locations of the concave portions.

2. The method according to claim 1, wherein the liquid resin is poured into the metal mold from a location removed from the locations where the concave portions are formed.

3. The method according to claim 1, wherein:
    the mold cavity extends in a longitudinal direction and includes first and second longitudinal ends; and
    the liquid resin is poured into the metal cavity from the first end of the mold cavity.

4. The method according to claim 2, wherein:
the mold cavity extends in a longitudinal direction and includes first and second longitudinal ends; and
the liquid resin is poured into the metal cavity from the first end of the mold cavity.

5. The method according to claim 3, wherein the convex portions are located closer to the first longitudinal end than the second longitudinal end.

6. The method according to claim 4, wherein the convex portions are located closer to the first longitudinal end than the second longitudinal end.

7. The method of claim 1, wherein a plane which is perpendicular to the central axis passes through each of the convex portions.

8. The method of claim 3, wherein the liquid resin is poured into the mold cavity in a direction which is parallel to the longitudinal direction.

9. The method of claim 4, wherein the liquid resin is poured into the mold cavity in a direction which is parallel to the longitudinal direction.

* * * * *